United States Patent
Fairley et al.

[11] Patent Number: 5,540,687
[45] Date of Patent: Jul. 30, 1996

[54] DEVICE FOR THE DISTRACTION OF BONES

[76] Inventors: Jeffrey D. Fairley, Haeberlstrasse 5, 80337 Munich; Jorg Bischof, Am Klosterwald 1 (One), 67808 Bennhausen, both of Germany

[21] Appl. No.: 246,656

[22] Filed: May 19, 1994

[30] Foreign Application Priority Data

May 19, 1993 [DE] Germany .................................. 5080037
May 19, 1994 [DE] Germany .......................... 43 16 794.2

[51] Int. Cl.⁶ .............................. A61B 17/68; A61B 17/60
[52] U.S. Cl. ............................... 606/60; 606/90; 606/105; 606/57
[58] Field of Search ..................... 606/60, 61, 57, 606/90, 105, 58, 69, 70, 71

[56] References Cited

U.S. PATENT DOCUMENTS

| | | | |
|---|---|---|---|
| 4,312,336 | 1/1982 | Danieletto et al. | 606/57 |
| 4,931,055 | 6/1990 | Bumpus et al. | 606/60 |
| 5,154,718 | 10/1992 | Cozad et al. | 606/61 |
| 5,364,396 | 11/1994 | Robinson et al. | 606/57 |

FOREIGN PATENT DOCUMENTS

| | | | |
|---|---|---|---|
| 3121271 | 5/1989 | Germany | 61/17 |
| 2168255 | 6/1986 | United Kingdom | 606/60 |

*Primary Examiner*—Stephen C. Pellegrino
*Assistant Examiner*—Scott B. Markow
*Attorney, Agent, or Firm*—Michael A. Glenn

[57] ABSTRACT

This invention relates to a device for the gradual distraction of bones, to be used especially in craniofacial dysostoses with early stenosis of the cranial sutures, comprising an internally threaded first sleeve intermeshing with an externally threaded spindle, which has an activating point. The spindle consists of an anterior extension, which slides into a second, unthreaded sleeve and rotates freely therein. The first sleeve is fitted with the first mounting plate, which rotates and features bore holes for the fixation via mini-screws to bone. The second sleeve embracing the spindle, is furnished with the holding elements for attachment in or to the bone.

5 Claims, 3 Drawing Sheets

DEVICE FOR THE DISTRACTION OF BONES

The present invention relates to a device for the distraction of bones in the craniofacial region or of the extremities of humans or animals, to be used especially in the treatment of midfacial retrusion, for instance craniofacial dysostoses, such as Apert's syndrome or Crouzon's disease, involving early stenosis of the cranial sutures, which are to be treated surgically in early childhood, i.e. at the age of 3 to 6 months.

Formerly, the conventional method used to remedy a stenosis of the cranial sutures, involved the resection of the affected cranial suture as well as the careful removal and lifting of both plates of the frontal bone (os frontale) after opening the scalp. All subsequent steps depend on which cranial suture is affected by early stenosis, or which syndrome the patient suffers from, for example Crouzon's disease or Apert's syndrome. In the case of isolated stenosis of the sutures, which does not affect the middle part of the face, only the suture affected by stenosis is resected. In so doing, the plate of the frontal bone is reshaped and reassembled to form one piece with a supra-orbital bar from the roof of the orbital cavity held together with absorbable suture material. The resultant advancement is fixed between the processus zygomaticus of the frontal bone and the temporal bone by means of mini-osteosynthesis plates and screws.

In the case of Crouzon's disease or Apert's syndrome, several sutures are affected by early stenosis. Consequently, not only the shape of the skull but also the midfacial retrusion has to be treated.

After resecting the suture and removing the plate of the frontal bone, the middle part of the face is mobilized. In so doing, the bone joints between the middle part of the face and the base of the skull are disjointed. Stabilisation is carried out as described above. As a rule, the surgery required is performed with the child aged 3 to 6 months. The osteosynthesis material is removed at 6 to 8 weeks, involving only a minor operation. Removal of the metal is meant to further the dynamic forces of brain growth.

The distraction device takes over the function of stabilizing the bone and at the same time is meant to facilitate midfacial distraction. Distraction is performed during a period of 6 to 8 weeks soon after implantation of the device, which will then be removed.

Formerly, the distraction of bones involved the positioning of two pins protruding through the skin of the patient, a so-called "fixateur externe". The pins harbour the danger of infection.

The conventional method has extraordinary disadvantages: the pins protruding through the skin of the patient pose a considerable risk of infection; the children have to lie in a supine position, and the parents are subject to serious psychological stress.

The present invention, therefore, is intended to provide a device for the said purpose, with the device being fixed subcutaneously to the bony skull and without pins protruding through the patient's skin. The said device, moreover, can also facilitate the subcutaneous correction of mandibular asymmetries treated in oral surgery, such as hemifacial microsomia (mandibulofacial dysostosis), or distraction surgery, such as that required following the amputation of an extremity, eg. thumb.

The present invention accomplishes this task through the use of a device for the gradual distraction of bones, to be used especially in craniofacial dysostoses with early stenosis of the cranial sutures, comprising an internally threaded first sleeve intermeshing with an externally threaded spindle, which has an activating point. The spindle consists of an anterior extension, which slides into a second, unthreaded sleeve and rotates freely therein. The first sleeve is fitted with the first mounting plate, which rotates and features bore holes for the fixation via mini-screws to bone. The second sleeve embracing the spindle, is furnished with the holding elements for attachment in or to the bone.

Thus, for example, in the above-mentioned treatment of midfacial retrusion with early stenosis of the cranial sutures, the usual fixation is implemented by means of mini-osteosynthesis plates. At the same time, for example, a pair of the distraction device as described is fixed, one behind each zygomatic arch of the os zygomaticum and to the squamous part of the temporal bone or the ala major of the sphenoid bone via mini-screws, which, for example, are made of titanium and are placed in position after bore holes are produced. Following the removal of the mini-plates, the activating point is exposed by means of a stab incision, the surgeon immediately starting mobilisation, which continues millimeter by millimeter until a distraction of ca. 3 cm i achieved.

The children are exposed to considerably less trauma than has hitherto been the case because the device is mounted subsequently. Parents of course accept this solution more readily, the frequency of operations is limited, and the risk of infection is considerably reduced.

In the least complex embodiment of the invention, the second sleeve slides onto the anterior extension of the spindle such that the latter may be activated in order to facilitate advancement without turning the sleeve. The desired positions for inserting the mini-screws to the bone are marked using the holes of the attachment on the first sleeve of the device, and are then prepared for fixing the device to bone as tightly as possible by means of the said mini-screws. Since the mounting plates are rotatable, they lie level with the bone.

The extension of the first sleeve after its attachment to bone leaves sufficient space behind the fixation allowing free access for activation of the spindle via screwdriver or wrench. Thus, the second sleeve moves forward. The second mounting plate is attached laterally or preferably along an extension of the length of the central axis of the device in order to avoid moments not desired during shearing stress. The said attachment, moreover, allows connection to a ball attachment that may be fixed and in addition provides a further degree of freedom by means of cardanic mounting.

The anterior extension itself may be used to hold the ball in position when sliding into the sleeve and pushing the ball against the fixed interface of the second sleeve, for example. Furthermore, the anterior extension may be surrounded by an inner sleeve, which can be moved in a forward direction by the anterior extension or the spindle, with the end of the inner sleeve embracing part of the ball and pushing it against the fixed interface, which is preferably flare-shaped towards the exterior.

The inner sleeve rotates freely in relation to the anterior extension and is conveniently fixed to the second sleeve through the use of screws, leaving a space between the sleeves and featuring hexagon- or bore hole-shaped recesses such that activation of the inner sleeve seizes the ball and with it the second mounting plate so that the device, even unloaded, is not subject to stress factors. Moreover, the anterior extension and/or the inner sleeve may be of flexible design, at least in the impact area between the sleeves, and may be made from elastic metal, for example, or of springs, which readily allow transfer of the required force onto the anterior mounting plate. Fixation of the ball could be further improved by using a ball having a shape made to fit the contour of the inner sleeve.

The entire device has a small diameter of a few millimeters so that the portion of skin covering it, is subjected to slight stretch. Materials to be considered are inert metals used in medicine (titanium) or even rigid plastics.

A further possibility of fashioning the holding element of the second sleeve consists in designing the sleeve as to have a self-cutting external thread, with the sleeve providing fixation to the zygomatic arch, for example. This design allows the anterior extension to rotate freely under thrust. This is an especially low-profile solution as it provides even closer contact between the entire device and the skull, and is of far greater advantage. In the case of the use of a fixed ball, the intermediate plate as elongation of the anterior extension engages the second sleeve 5 wherein the second mounting plate is of course dispensed with.

Since the bone into which the mini-screws are inserted is uneven, one should consider adjustable elastic pads to smooth out the unevenness of the bone, thus increasing surface pressure. Since mainly relatively small torques have to be transferred, a further embodiment of the device might include an electrical motor being activated by remote control (radio signals) in order to provide the forces required.

The present invention will now be described with reference to the accompanying drawings in which.

Figure 1:
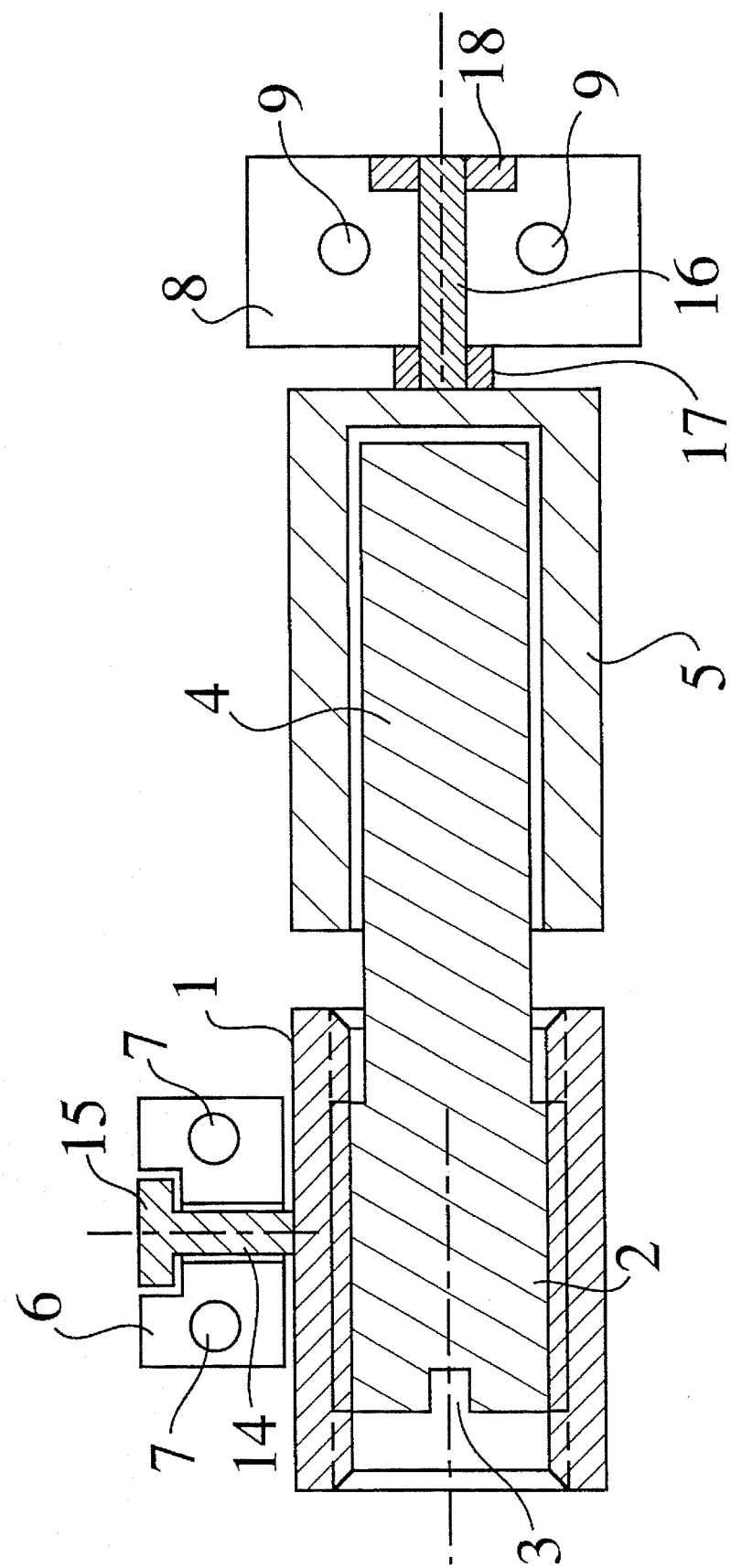
FIG. 1 shows a longitudinal section of the device according to invention.

FIG. 1 shows a greatly enlarged view of the internally threaded first sleeve 1. The said sleeve holds an externally threaded spindle 2 featuring an activating point 3 for a screwdriver or designed as a hexagon socket for an Allan key. The spindle 2 comprises an anterior extension 4, which rotates freely in a separate second sleeve 5, with the anterior extension 4 fitting closely, i.e. with little play, inside the second sleeve, and the free end of the anterior extension 4 pushing the second sleeve 5 forward according to the pitch of the thread on turning the activating point 2. A first mounting plate 6 with bore holes 7 revolves on a pin 14 attached to the first sleeve 1, and is held in position by a securing plate.

There is also a pin 16 at the end of the second sleeve 5, which is preferably attached coaxially, and on which a second mounting plate 8 with bore holes 9 revolves. Between these, a spacer block 17 and a securing plate 18 are placed.

Figure 2:
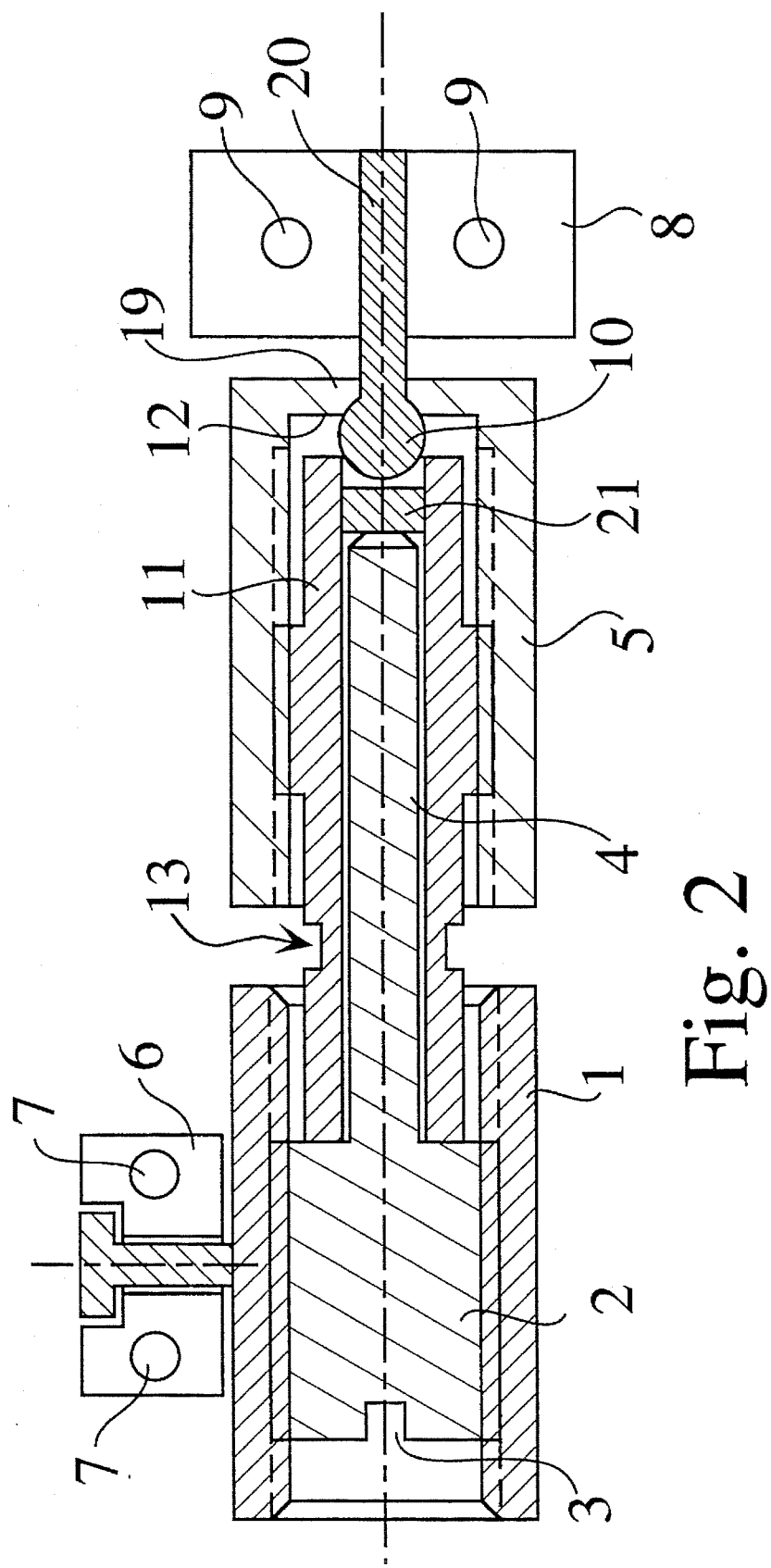
FIG. 2 shows one embodiment of the present invention.

FIG. 2 illustrates an embodiment of the invention designed such that the second mounting plate 8 is mounted to provide a universal joint and can be fixed in the desired position.

The end of the second sleeve, moreover, features a fixed interface 12 with a cone-shaped opening 19. The sleeve holds a ball 10 connected to the second mounting plate 8 via an intermediate plate 20. In the most simple example, the anterior extension 4—when moving forward after attachment to the bone in question—pushes against the ball 10, which can be profiled, thus holding it in position between the extension itself and the inner edge of the opening 19.

Instead of a rod-like anterior end 4, its function can be substituted by an inner sleeve 11 such that it is linked to the spindle 2 in one piece, and the end of the inner sleeve clamps the ball 10 as depicted.

The most efficient solution, however, is screwing the externally threaded inner sleeve 11 into the concomitant internal thread of the second sleeve 5. The said inner sleeve features recesses 13 between the first sleeve 1 and the second sleeve 5, which are designed as a hexagon insert to be engaged by an open-jawed wrench, or, for instance, in the form of several radially distributed bore holes to be turned gradually by means of a gudgeon. A recess 13 of similar nature may be implemented on the second sleeve 5, too. The inner sleeve 11 may be pushed against the spindle 2 in order to transfer thrust onto the second mounting plate 8, which is firmly connected to the intermediate plate 20. Shifted in a slightly backward direction, a contact block 21, which is solved into the inner sleeve at one of its ends and which may be pushed against the end of the anterior extension 4 may fulfil the same purpose. The anterior extension 4 may be secured to the inner sleeve 11, for example with an endless radial groove and tongue, such that it can rotate. In the present embodiment of the invention the anterior extension 4 slides in its entire length into the inner sleeve 11 such that the parts are also firmly held in position due to the friction prevailing.

Figure 3:
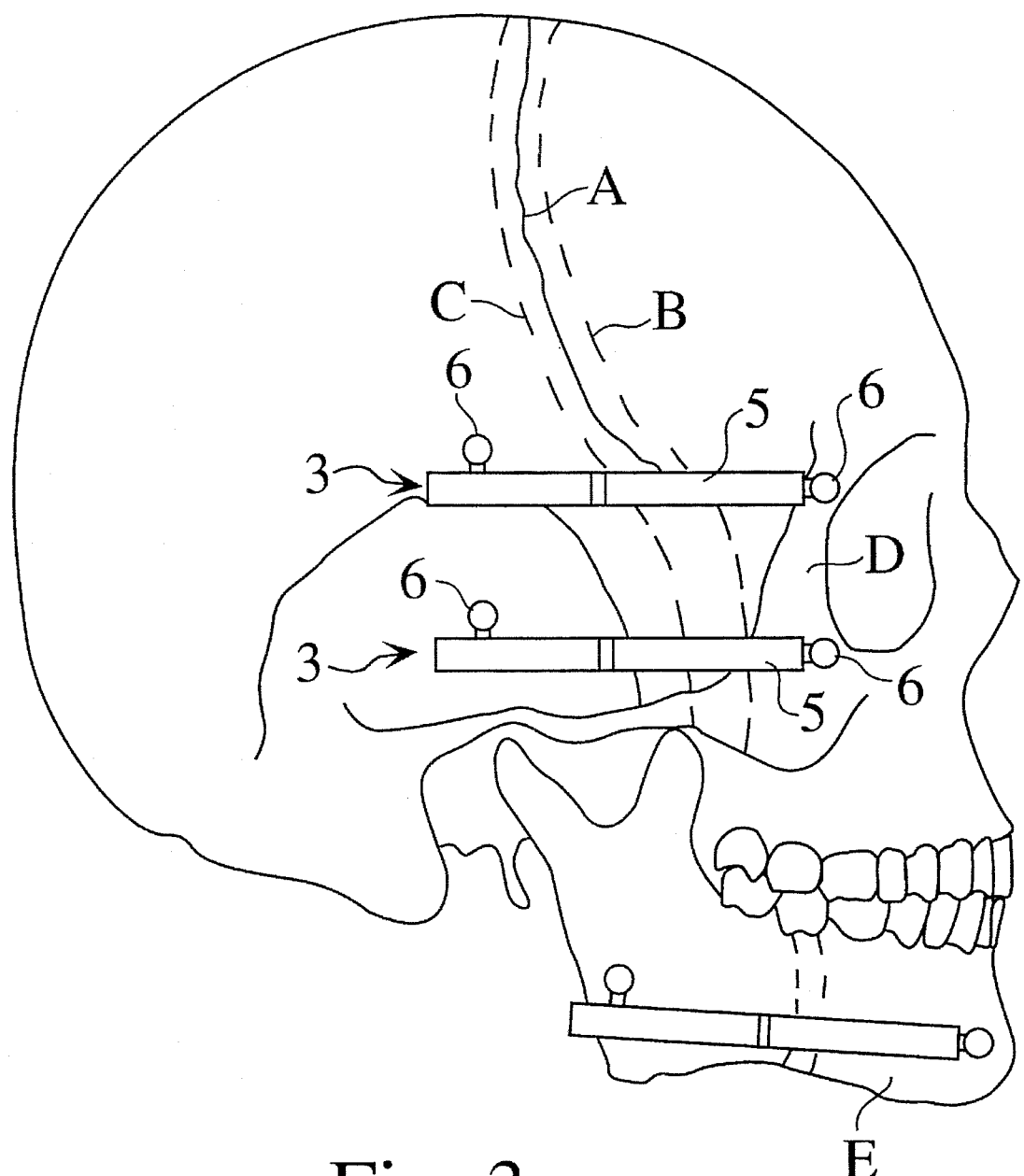
FIG. 3 illustrates an application by way of example.

FIG. 3 shows a lateral view of the skull in which the stenosed coronal suture A is removed by means of two incisions B and C. Two distraction devices according to invention are fixed to the zygomatic arch (os zygomaticum) D by means of the second mounting plates 8 and to the temporal bone by means of the first mounting plates 6 through the use of self-cutting mini-screws lying underneath. The second sleeves 5 can be moved in a forward direction by way of engaging the activating points 3 in order to gradually increase the distance between the incisions B and C.

A further application of this device according to the invention is its use in the distraction of a mandible.

We claim:

1. A device that is adapted for subcutaneous fixation to a patient's skull for gradual distraction of bones in craniofacial dysostoses with early stenosis of the cranial sutures, comprising:

a first sleeve having internal threads, the first sleeve holding a spindle having an activating point and having an external thread that intermeshes with the internal thread of the first sleeve;

a second sleeve, said spindle including an extension that is surrounded by, but not secured to, said second sleeve and that rotates freely within said second sleeve;

a first mounting plate fitted to said first sleeve and being arranged for rotation relative thereto, said first mounting plate including bore holes formed therethrough and being adapted for fixation to a patient's skull at a first location with mini-screws; and a holding element fitted to said second sleeve and being arranged for rotation relative thereto, wherein said holding element further comprises a second mounting plate, said second mounting plate including bore holes formed therethrough and being adapted for fixation to a patient's skull at said second location with miniscrews, wherein said second mounting plate is arranged in a coaxial position in relation to said extension and is affixed to an end of said second sleeve as a universal joint.

2. A device that is adapted for subcutaneous fixation to a patient's skull for gradual distraction of bones in craniofacial dysostoses with early stenosis of the cranial sutures, comprising;

a first sleeve having internal threads, the first sleeve holding a spindle having an activating point and having an external thread that intermeshes with the internal thread of the first sleeve;

a second sleeve, said spindle including an extension that is surrounded by, but not secured to, said second sleeve and that rotates freely within said second sleeve;

a first mounting plate fitted to said first sleeve and being arranged for rotation relative thereto, said first mounting plate including bore holes formed therethrough and being adapted for fixation to a patient's skull at a first location with mini-screws; and a holding element fitted to said second sleeve and being arranged for rotation relative thereto, wherein said holding element further comprises a second mounting plate, said second mounting plate including bore holes formed therethrough and being adapted for fixation to a patient's skull at sai second location with mini-screws, wherein said second mounting plate is connected to a ball via an intermediate plate, and wherein said second mounting plate is locked by an inner sleeve that is positioned with said second sleeve and which is axially movable within said second sleeve to push an end of said inner sleeve against said ball and force said ball against an inner surface of an end of said second sleeve, said intermediate plate projecting through an aperture formed through said second sleeve inner end, said aperture having a cone shape that is narrower at said inner surface of said end of said second sleeve and that flares away from said inner surface of said end of said second sleeve to an outer surface of said end of said second sleeve.

3. The device of claim 2, wherein said spindle further comprises an extension that is rotatable within said inner sleeve, said inner sleeve further comprising an external thread, said second sleeve having an internal thread that intermeshes with the external thread of said inner sleeve; the inner sleeve in a region between said first sleeve and said second sleeve further comprising at least one recess adapted to provide an activating point, wherein said ball is placed in a desired position between said inner sleeve and said inner surface of said end of said second sleeve by operation of said activating point.

4. The device of claim 2, wherein said ball is shaped to fit a contour of said inner sleeve.

5. The device of claim 2, wherein at least one of said extension and said inner sleeve are flexible in a region between said first sleeve and said second sleeve.

* * * * *